US009688767B2

(12) United States Patent
Mallat et al.

(10) Patent No.: US 9,688,767 B2
(45) Date of Patent: Jun. 27, 2017

(54) METHOD OF PREDICTING SURVIVAL TIME IN MYOCARDIAL INFARCTION PATIENTS BY MEASURING BAFF LEVELS

(71) Applicants: INSERM (Institut National de la Sante et de la Recherche Medicale, Paris (FR); Universite Paris Descartes, Paris (FR); Universite Pierre et Marie Curie—UPMC, Paris (FR); Assistance Publique—Hopitaux de Paris (APHP), Paris (FR)

(72) Inventors: Ziad Mallat, Paris (FR); Alain Tedgui, Paris (FR); Tabassome Simon, Paris (FR); Nicolas Danchin, Paris (FR)

(73) Assignees: Institut National de la Sante et de la Recherche Medicale (INSERM), Paris (FR); Universite Paris Descartes, Paris (FR); Universite Pierre et Marie Curie-UPMC, Paris (FR); Assistance Publique-Hopitaux de Paris (APHP), Paris (FR)

(*) Notice: Subject to any disclaimer, the term of this patent is extended or adjusted under 35 U.S.C. 154(b) by 0 days.

(21) Appl. No.: 14/776,029

(22) PCT Filed: Mar. 14, 2014

(86) PCT No.: PCT/EP2014/055059
§ 371 (c)(1),
(2) Date: Sep. 14, 2015

(87) PCT Pub. No.: WO2014/140243
PCT Pub. Date: Sep. 18, 2014

(65) Prior Publication Data
US 2016/0024218 A1    Jan. 28, 2016

(30) Foreign Application Priority Data

Mar. 15, 2013 (EP) .................................. 13305299

(51) Int. Cl.
*A61K 39/395* (2006.01)
*C07K 16/28* (2006.01)
*C07K 14/525* (2006.01)
*C07K 14/705* (2006.01)
*C07K 14/715* (2006.01)
*G01N 33/53* (2006.01)
*G01N 33/68* (2006.01)
*C12Q 1/68* (2006.01)
*A61K 39/00* (2006.01)

(52) U.S. Cl.
CPC ...... *C07K 16/2878* (2013.01); *C07K 16/2875* (2013.01); *C12Q 1/6883* (2013.01); *G01N 33/6872* (2013.01); *A61K 39/3955* (2013.01); *A61K 2039/505* (2013.01); *C07K 14/525* (2013.01); *C07K 2317/76* (2013.01); *C12Q 2600/118* (2013.01); *C12Q 2600/158* (2013.01); *G01N 33/53* (2013.01); *G01N 2333/70575* (2013.01); *G01N 2800/324* (2013.01); *G01N 2800/52* (2013.01)

(58) Field of Classification Search
CPC .......... A61K 2300/00; A61K 2039/505; A61K 39/395; A61K 39/3955; C07K 16/2887; C07K 16/2875; C07K 16/2878; C07K 16/28; C07K 16/00; C07K 16/18; C07K 14/705; C07K 14/7056; C07K 14/70596
See application file for complete search history.

(56) References Cited

U.S. PATENT DOCUMENTS

2003/0223996 A1    12/2003   Ruben et al.
2005/0048626 A1     3/2005   Desjarlais et al.

FOREIGN PATENT DOCUMENTS

WO       0216411 A2       2/2002
WO     2005042009 A1      5/2005

OTHER PUBLICATIONS

Ait-Oufella et al. B-Cell depletion reduces development of atherosclerosis in mice. Arterioscl Thrombosis Vascular Biol 2010 Scientific Sessions: e271, abstract #P473, Apr. 2010.*
Ait-Oufella et al. B cell depletion reduces the development of atherosclerosis in mice. J Exp Med 207(8): 1579-1587, 2010.*
Arunprasath et al. Rituximab induced myocardial infarction: a fatal drug reaction. J Cancer Res Therapeutics 7(3): 346-348, 2011 (2 total pages).*
Haas et al. Anti-CD20 therapy for heart attack. SciBX 6(37): 1-3; Sep. 26, 2013.*
Mehrpooya et al. Delayed myocardial infarction associated with rituximab infusion: a case report and literature review. Am J Therapeutics 23: e283-e287, 2016.*
Poterucha et al. Rituximab-induced polymorphic ventricular tachycardia. Tex Heart Inst J 37(2): 218-220, 2010.*

(Continued)

*Primary Examiner* — Bridget E Bunner
(74) *Attorney, Agent, or Firm* — Whitham Curtis & Cook, PC

(57) ABSTRACT

The present invention relates to a method for predicting the survival time of a patient suffering from myocardial infarction or the recurrence of a myocardial infarction. The method comprises the steps of i) determining the expression level of BAFF in a sample from the patient, ii) comparing the expression level with a predetermined reference value and iii) providing a good prognosis of the survival time or a low risk of the recurrence of a myocardial infarction when the expression level is lower than the predetermined reference value and a poor prognosis of the survival time or a high risk of the recurrence of a myocardial infarction when the expression level is higher than the predetermined reference value.

3 Claims, 4 Drawing Sheets

(56) References Cited

OTHER PUBLICATIONS

Prabhu et al. The biological basis for cardiac repair after myocardial infarction. Circ Res 119: 91-112, 2016.*
van Silj et al. Myocardial infarction after rituximab treatment for rheumatoid arthritis: is there a link? Curr Pharm Designs 20: 496-499, 2014.*
Zouggari et al. B lymphocytes trigger monocyte mobilization and impair heart function after acute myocardial ischemia. Nature Med 19(10): 1273-1280, plus 2 pages of online supplemental material; published online Sep. 15, 2013.*
Zouggari et al. B lymphocyte trigger MCP3-dependent mobilization and promote adverse ventricular remodeling after myocardial infarction. Archives Cardiovascul Diseases Suppl 4(Suppl 1): p. 11, abstract #0170.*
Kahn et al., "Prevention of Murine Antiphospholipid Syndrome by BAFF Blockade", Arthritis and Rheumatism, Sep. 1, 2008, vol. 58, No. 9, p. 2824-2834.

* cited by examiner

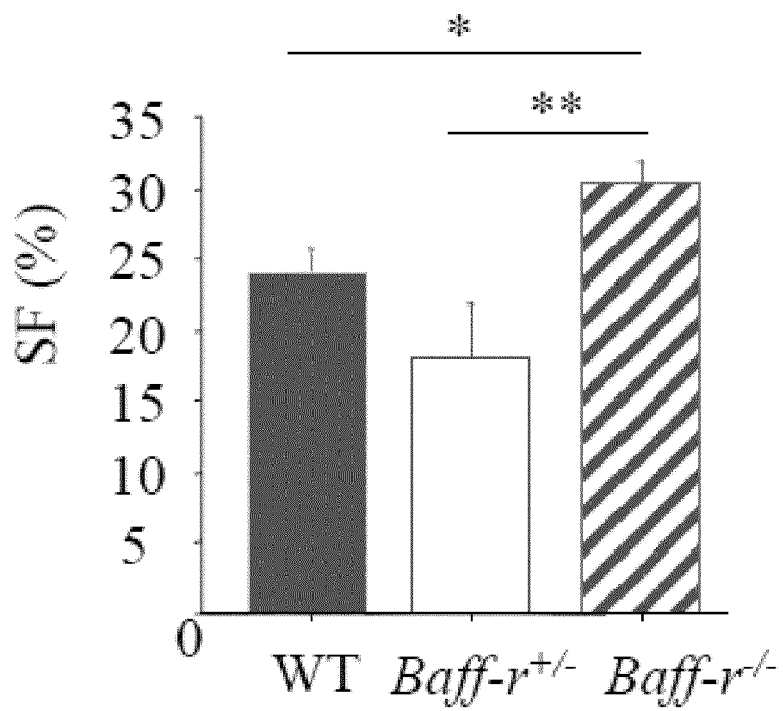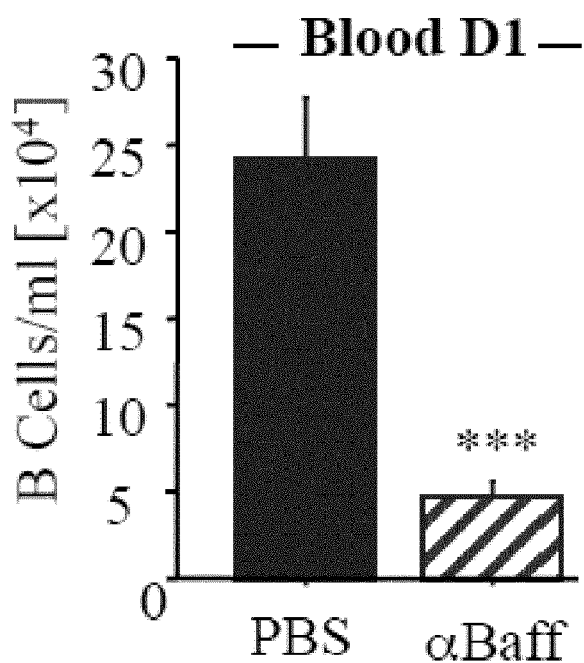
Figure 2 B and C

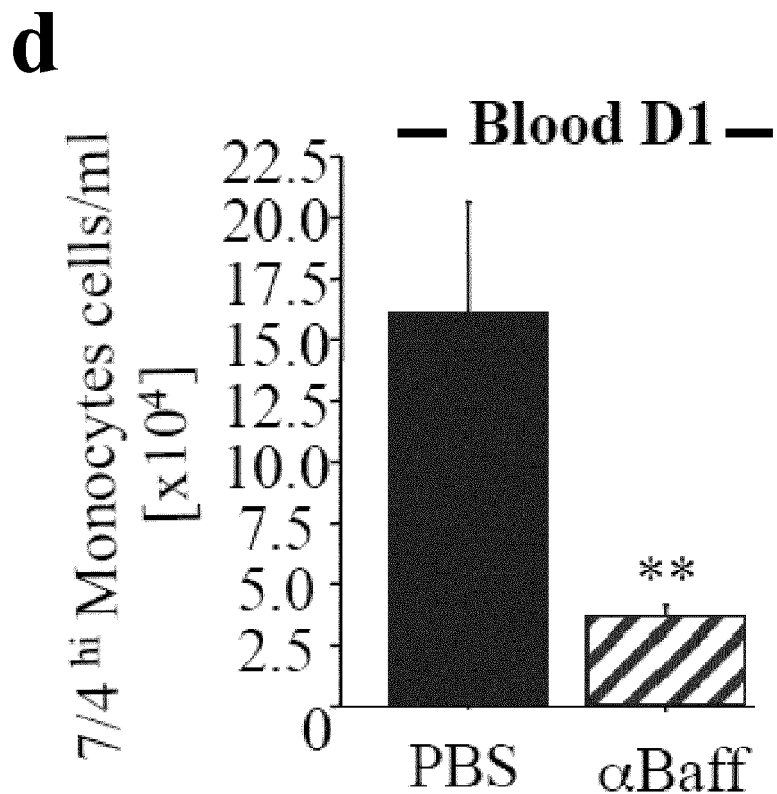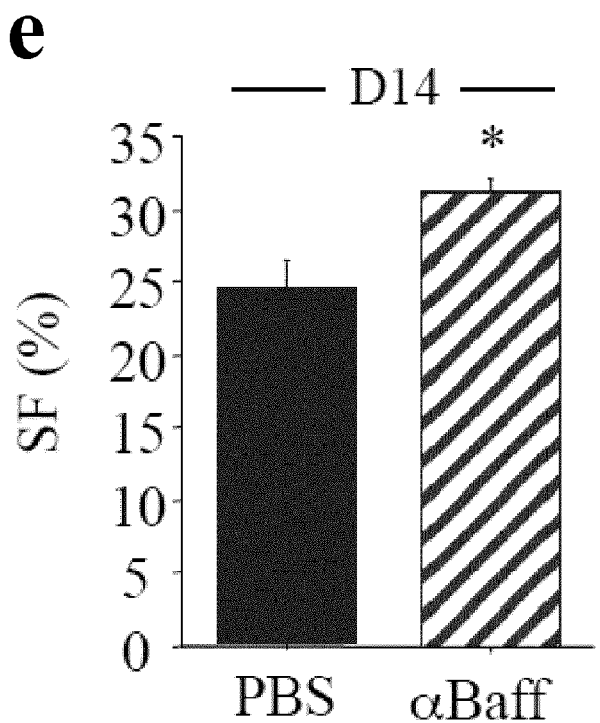
Figure 2 D and E

METHOD OF PREDICTING SURVIVAL TIME IN MYOCARDIAL INFARCTION PATIENTS BY MEASURING BAFF LEVELS

FIELD OF THE INVENTION

The present invention relates to a method for predicting the survival time of a patient suffering of myocardial infarction or the recurrence of a myocardial infarction in a patient who has suffered from a myocardial infarction comprising the steps consisting of i) determining the expression level of BAFF in a sample from said patient, ii) comparing said expression level with a predetermined reference value and iii) providing a good prognosis of the survival time or a low risk of the recurrence of a myocardial infarction when the expression level is lower than the predetermined reference value and a poor prognosis of the survival time or a high risk of the recurrence of a myocardial infarction when the expression level is higher than the predetermined reference value.

BACKGROUND OF THE INVENTION

Acute thrombotic obstruction of the blood flow in a coronary artery precipitates myocardial infarction. The loss of heart muscle in the necrotic zone and the compromised function of the remaining viable cardiomyocytes of the peri-necrotic region initiate a series of events that, if unopposed, frequently lead to adverse remodeling of the heart chamber, precipitating heart failure. The mainstay of treatment of acute myocardial infarction (MI) associates rapid restoration of a patent coronary artery either mechanically or through thrombolytic and anti-platelet therapies, and administration of agents that reduce oxygen consumption and unload the heart muscle. The wide use of this therapeutic strategy has led to significant reductions in both morbidity and mortality after acute MI [White, H. D et al., 2008]. Still, the clinical and social burden of ischemic heart disease is unacceptably high and the efficacy of additional anti-thrombotic therapies is often mitigated by the increased risk of hemorrhagic events. Thus, efforts are being directed towards targeting other pathophysiological pathways, particularly those involved in post-ischemic cardiac remodelling [Shah, A. M et al., 2011].

The immune system becomes activated in response to myocardial damage. Shortly after ischemia, the damaged tissue exposes ligands that are recognized by components of the innate immune system, which leads to its activation. For example, non-myosin heavy chain type II A and C are exposed following ischemia/reperfusion injury and recognized by natural IgM antibodies, leading to activation of mannan binding lectin and serum complement, which aggravates tissue injury. C-reactive protein (CRP), a short pentraxin acute-phase protein, also binds to damaged tissue and activates the complement, leading to aggravation of tissue injury in the setting of acute MI 13. In contrast, long pentraxin 3, a molecule that limits complement activation plays a cardioprotective role in this setting. The acute inflammatory response also leads to the mobilization and recruitment of innate immune cells. Few hours after the ischemic insult, neutrophils are actively recruited into the ischemic tissue and contribute to tissue inflammation and cardiovascular injury through the production of inflammatory mediators, reactive oxygen species and various proteases [Granger, D. N. et al, 1995 and Vinten-Johansen, J 2004]. The wave of neutrophil infiltration is followed by the mobilization and recruitment of monocytes. Recent studies have shed new light on the mechanisms of monocytes recruitment and life cycle in the setting of acute MI, and suggested differential pathogenic or protective roles for Ly6Chi and Ly6Clo monocytes, respectively, in cardiac remodeling and preservation of heart function [Nahrendorf, M., et al, 2007 and Leuschner, F., et al, 2012]. Despite this increasing knowledge, the utility of targeting the immune response in this setting is still uncertain as revealed by the lack of efficacy of complement inhibition in patients with acute MI [Mahaffey, K. W., et al, 2003; Granger, C. B., et al, 2003; Armstrong, P. W., et al, 2007 and Eikelboom, J. W et al, 2007]. Thus, a better characterization of the determinants of the immune response following ischemic injury and the mechanisms by which they contribute to tissue damage is required in order to fill the existing gap of knowledge that limits clinical translation, and design efficient therapeutic strategies for future use in humans.

SUMMARY OF THE INVENTION

Here, the inventors addressed the interactions between mature B lymphocytes and other innate myeloid cells in the setting of ischemic injury. They show in a cohort of 1000 patients admitted for acute myocardial infarction that the circulating level of BAFF is elevated and is associated with adverse cardiovascular outcome. Moreover, they show that inhibition of BAFF signalling impairs monocyte mobilization and improves heart function after acute myocardial infarction.

Thus, the present invention relates to a method for predicting the survival time of a patient suffering of myocardial infarction or the recurrence of a myocardial infarction in a patient who has suffered from a myocardial infarction comprising the steps consisting of i) determining the expression level of BAFF in a sample from said patient, ii) comparing said expression level with a predetermined reference value and iii) providing a good prognosis of the survival time or a low risk of the recurrence of a myocardial infarction when the expression level is lower than the predetermined reference value and a poor prognosis of the survival time or a high risk of the recurrence of a myocardial infarction when the expression level is higher than the predetermined reference value.

The invention also relates to a compound which inhibits the binding of BAFF to TACI, BCMA or BAFF-R or a compound which is an inhibitor of BAFF, TACI, BCMA or BAFF-R gene expression for use in the improvement of heart function.

DETAILED DESCRIPTION OF THE INVENTION

Definitions

Figure 1:
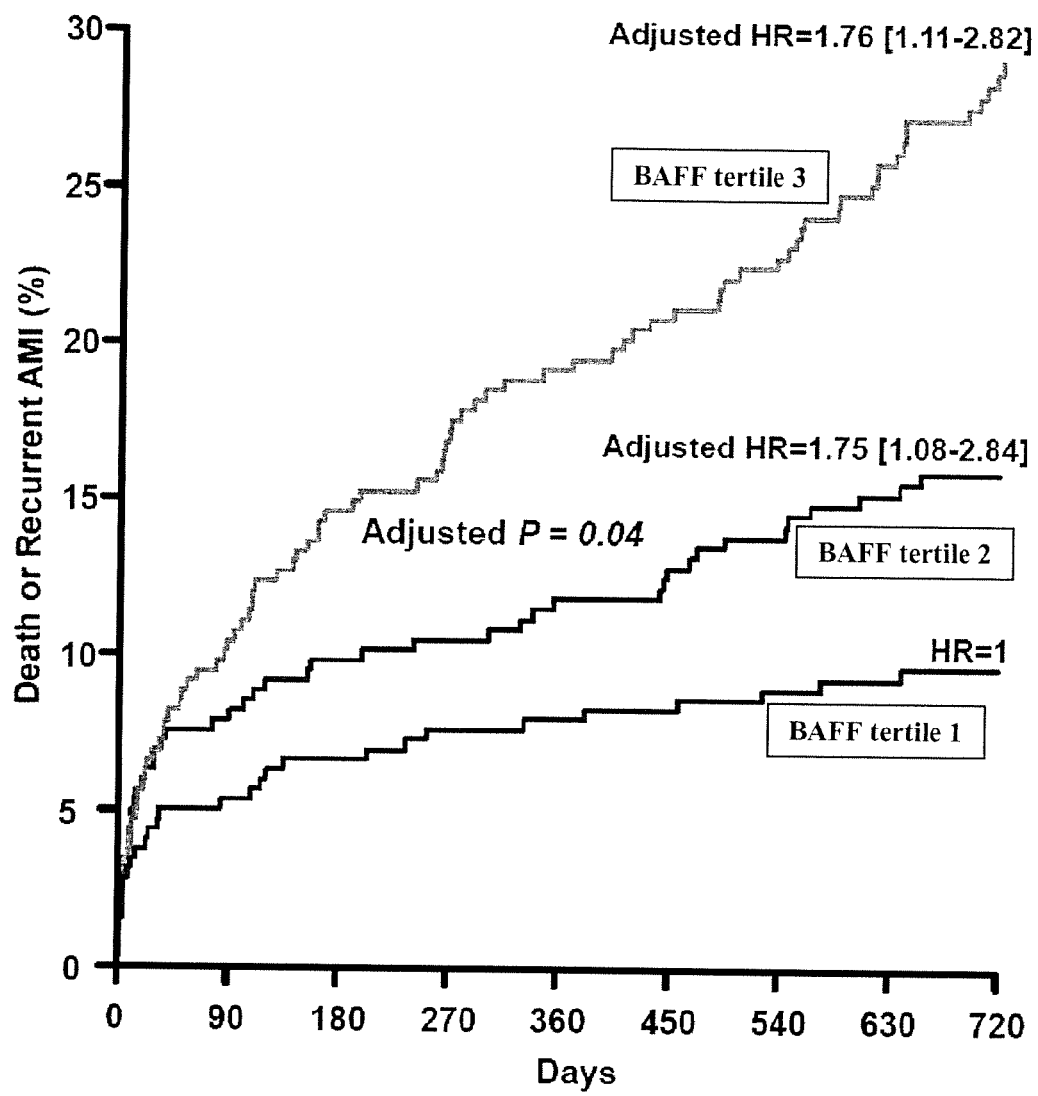
FIG. 1. Circulating level of Baff at the acute phase of MI are associated with cardiovascular outcomes. The probability of outcome events (death or recurrent MI) as a function of baseline circulating Baff level in patients with acute MI. Detectable high level of Baff at the admission for acute MI were independently predictive of death and recurrent MI after two years of follow-up after multiple adjustments (see Methods). HR=Hazard ratio.

Throughout the specification, several terms are employed and are defined in the following paragraphs.

Prognostic Method

The invention relates to a method for predicting the survival time of a patient suffering of myocardial infarction or the recurrence of a myocardial infarction in a patient who has suffered from a myocardial infarction comprising the steps consisting of i) determining the expression level of BAFF in a sample from said patient, ii) comparing said expression level with a predetermined reference value and iii) providing a good prognosis of the survival time or a low risk of the recurrence of a myocardial infarction when the expression level is lower than the predetermined reference value and a poor prognosis of the survival time or a high risk of the recurrence of a myocardial infarction when the expression level is higher than the predetermined reference value.

In one embodiment, the myocardial infarction may be an acute myocardial infarction.

Typically, the sample according to the invention may be a blood, plasma, serum, lymph and cardiac tissue.

As used herein, the term "BAFF" (B cell activating factor), also known as BlyS (B lymphocyte stimulator) has its general meaning in the art and denotes a cytokine that belongs to the tumor necrosis factor (TNF) ligand family. This cytokine is a ligand for three receptors: TNFRSF13B/TACI, TNFRSF17/BCMA, and TNFRSF13C/BAFF-R (see for example Cancro P. Michael et al., 2009). This cytokine is expressed in myeloid and lymphoid B cell lineage cells, and acts as a potent B cell activator. It has been also shown to play an important role in the proliferation and differentiation of B cells. An exemplary sequence for human BAFF protein is deposited in the UniProtKB/Swiss-Prot database under accession numbers Q9Y275.

As used herein, the term "patient", is intended for a human affected or likely to be affected with a myocardial infarction, particularly an acute myocardial infarction.

In one embodiment, the patient is a non-lupic patient. According to the invention, a "non-lupic patient" denotes a patient which is not affected by a lupus but which is affected or which is intended to be affected by a myocardial infarction and particularly by an acute myocardial infarction.

Thus, In a particular embodiment, the invention relates to a method for predicting the survival time of a non-lupic patient suffering of myocardial infarction or the recurrence of a myocardial infarction in a non-lupic patient who has suffered from a myocardial infarction comprising the steps consisting of i) determining the expression level of BAFF in a sample from said patient, ii) comparing said expression level with a predetermined reference value and iii) providing a good prognosis of the survival time or a low risk of the recurrence of a myocardial infarction when the expression level is lower than the predetermined reference value and a poor prognosis of the survival time or a high risk of the recurrence of a myocardial infarction when the expression level is higher than the predetermined reference value.

The term "determining the expression level of BAFF" as used above includes qualitative and/or quantitative detection (measuring levels) with or without reference to a control. Typically BAFF expression may be measured for example by RT-PCR, immunohistochemistry or ELISA performed on the sample.

The "control" or the "reference value" may be a healthy subject, i.e. a subject who does not suffer from any myocardial infarction. The control may also be a subject suffering from myocardial infarction. Preferably, said control is a healthy subject.

For example determining the expression level of BAFF in sample may be performed by measuring the expression level of BAFF gene.

Typically, the detection comprises contacting the sample with selective reagents such as probes, primers or ligands, and thereby detecting the presence, or measuring the amount, of polypeptides or nucleic acids of interest originally present in the sample. Contacting may be performed in any suitable device, such as a plate, microtiter dish, test tube, well, glass, column . . . . In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the sample.

In a particular embodiment, the expression level of BAFF gene may be determined by determining the quantity of mRNA of BAFF gene. Such method may be suitable to measure the expression level of BAFF gene in the sample.

Methods for measuring the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA may be then detected by hybridization (e.g., Northern blot analysis).

Alternatively, the extracted mRNA may be subjected to coupled reverse transcription and amplification, such as reverse transcription and amplification by polymerase chain reaction (RT-PCR), using specific oligonucleotide primers that enable amplification of a region in the BAFF gene. Preferably quantitative or semi-quantitative RT-PCR is used. Real-time quantitative or semi-quantitative RT-PCR is particularly advantageous. Extracted mRNA may be reverse-transcribed and amplified, after which amplified sequences may be detected by hybridization with a suitable probe or by direct sequencing, or any other appropriate method known in the art.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably at least 85% identical and even more preferably at least 90%, preferably at least 95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

In a particular embodiment, the method of the invention comprises the steps of providing total RNAs obtained from the sample of the patient, and subjecting the RNAs to amplification and hybridization to specific probes, more particularly by means of a quantitative or semi-quantitative RT-PCR.

Total RNAs can be easily extracted from the sample. For instance, the sample may be treated prior to its use, e.g. in order to render nucleic acids available. Techniques of cell or protein lysis, concentration or dilution of nucleic acids, are known by the skilled person.

In another embodiment, the expression level of BAFF gene may be measured by DNA microarray analysis. Such DNA microarray or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To measure the expression level of BAFF gene, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

Detection of BAFF expression in the sample may also be performed by measuring the level of BAFF protein. In the present application, the "level of BAFF protein" means the quantity or concentration of said BAFF protein or the quantity of cells which express BAFF. Such methods comprise contacting a sample with a binding partner capable of selectively interacting with BAFF protein present in the sample. The binding partner is generally an antibody that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith. More preferably, determination of the concentrations of BAFF is performed with a fluorescence-activated cell sorter (FACS). Said fluorescence-activated cell sorter is a machine that can rapidly separate the cells in a suspension on the basis of size and the color of their fluorescence.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with a set of antibodies against the proteins to be tested. A sample containing or suspected of containing the marker protein is then added to the coated wells. After a period of incubation sufficient to allow the formation of antibody-antigen complexes, the plate(s) can be washed to remove unbound moieties and a detectably labeled secondary binding molecule is added. The secondary binding molecule is allowed to react with any captured sample marker protein, the plate is washed and the presence of the secondary binding molecule is detected using methods well known in the art.

preferred particular method utilizes immunohistochemistry, a staining method based on immunoenzymatic reactions using monoclonal or polyclonal antibodies to detect cells or specific proteins such as tissue antigens. Typically, immunohistochemistry protocols involve at least some of the following steps:

1) antigen retrieval (eg., by pressure cooking, protease treatment, microwaving, heating in appropriate buffers, etc.);

2) application of primary antibody (i.e. anti-BAFF protein antibody) and washing;

3) application of a labeled secondary antibody that binds to primary antibody (often a second antibody conjugate that enables the detection in step 5) and wash;

4) an amplification step may be included;

5) application of a detection reagent (e.g. chromagen, fluorescently tagged molecule or any molecule having an appropriate dynamic range to achieve the level of or sensitivity required for the assay);

6) counterstaining may be used and 7) detection using a detection system that makes the presence of the proteins visible (to either the human eye or an automated analysis system), for qualitative or quantitative analyses.

Various immunoenzymatic staining methods are known in the art for detecting a protein of interest. For example, immunoenzymatic interactions can be visualized using different enzymes such as peroxidase, alkaline phosphatase, or different chromogens such as DAB, AEC, or Fast Red; or fluorescent labels such as FITC, Cy3, Cy5, Cy7, Alexafluors, etc. Counterstains may include H&E, DAPI, Hoechst, so long as such stains are compatable with other detection reagents and the visualization strategy used. As known in the art, amplification reagents may be used to intensify staining signal. For example, tyramide reagents may be used. The staining methods of the present invention may be accomplished using any suitable method or system as would be apparent to one of skill in the art, including automated, semi-automated or manual systems.

The method of the invention comprises a step consisting of comparing BAFF expression with a reference value or a control reference.

Predetermined reference values used for comparison may consist of "cut-off" values that may be determined as described hereunder. Reference ("cut-off") value for BAFF expression may be determined by carrying out a method comprising the steps of:

a) providing a collection of samples from patients suffering of myocardial infarction;

b) determining the BAFF expression level for each sample contained in the collection provided at step a);

c) ranking the samples according to said expression level d) classifying said samples in subsets of increasing, respectively decreasing, number of members ranked according to their expression level, e) providing, for each sample provided at step a), information relating to the actual clinical outcome for the corresponding patient (i.e. the survival time of a patient suffering of myocardial infarction or the recurrence of a myocardial infarction or both);

f) for each pair of subsets of samples, obtaining a Kaplan Meier percentage of survival curve;

g) for each subsets of samples calculating the statistical significance (p value) between both subsets h) selecting as reference value for the expression level, the value of expression level for which the p value is the smallest.

A confidence interval may be constructed around the value of expression level thus obtained, for example ±5 or 10%.

For example the expression level of BAFF has been assessed for 100 samples of 100 patients. The 100 samples are ranked according to the expression level of BAFF. Sample 1 has the highest expression level and sample 100 has the lowest expression level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding patient, Kaplan Meier curves are prepared for each of the 99 groups of two subsets. Also for each of the 99 groups, the p value between both subsets was calculated.

The reference value is selected such as the discrimination based on the criterion of the minimum p value is the strongest. In other terms, the expression level corresponding to the boundary between both subsets for which the p value is minimum is considered as the reference value. It should be noted that according to the experiments made by the inventors, the reference value is not necessarily the median value of expression levels.

In routine work, the reference value (cut-off value) may be used in the present method to discriminate samples and therefore the corresponding patients.

Kaplan-Meier curves of percentage of survival as a function of time are commonly used to measure the fraction of patients living for a certain amount of time after treatment and are well known by the man skilled in the art. P value is conventionally used in statistical significance testing.

The man skilled in the art also understands that the same technique of assessment of the expression level of BAFF should preferably be used for obtaining the reference value and thereafter for assessment of the expression level of BAFF of a patient subjected to the method of the invention.

If for example, the expression level of BAFF is higher than the reference value, the patient is considered as a poor prognosis of the survival time or as a high risk of the recurrence of a myocardial infarction. Similarly, the expression level of BAFF is lower than the reference value, the patient is considered as a good prognosis of the survival time or as a low risk of the recurrence of a myocardial infarction.

The setting of a single "cut-off" value allows discrimination between a poor and a good prognosis with respect to survival time and a low risk and a high risk of the recurrence of a myocardial infarction for a patient. Practically, high statistical significance values (e.g. low P values) are generally obtained for a range of successive arbitrary quantification values, and not only for a single arbitrary quantification value. Thus, in one alternative embodiment of the invention, instead of using a definite reference value, a range of values is provided.

Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. According to this specific embodiment of a "cut-off" value, poor, good prognosis or recurrence can be determined by comparing the expression level with the range of values which are identified. In certain embodiments, a cut-off value thus consists of a range of quantification values, e.g. centered on the quantification value for which the highest statistical significance value is found (e.g. generally the minimum P value which is found). For example, on a hypothetical scale of 1 to 10, if the ideal cut-off value (the value with the highest statistical significance) is 5, a suitable (exemplary) range may be from 4-6.

Therefore, a patient may be assessed by comparing values obtained by measuring the expression level of BAFF, where values less than 5 reveal a good prognosis and values greater than 5 reveal a poor prognosis. In a another embodiment, a patient may be assessed by comparing values obtained by measuring the expression level of BAFF and comparing the values on a scale, where values below the range of 4-6 indicate a good prognosis and values above the range of 4-6 indicate a poor prognosis, with values falling within the range of 4-6 indicating an intermediate prognosis.

In a particular embodiment, the method of the invention comprises comparison steps which include a classification of the quantification values measured for the expression level of BAFF into two possibilities, respectively: (i) a first possibility when the quantification value for the expression level is higher than the predetermined corresponding reference value (the first possibility is named "Hi" for example) and (ii) a second possibility when the quantification value for the expression level is lower than the predetermined corresponding reference value (the second possibility is named "Lo" for example).

As used herein, "the expression level of BAFF" refers to an amount or a concentration of a transcription product, for instance mRNA coding for BAFF, or of a translation product, for instance the protein BAFF or of percentage of cells which express BAFF or of mean fluorescence intensity of BAFF (by FACS). Typically, a level of mRNA expression can be expressed in units such as transcripts per cell or nanograms per microgram of tissue. A level of a polypeptide can be expressed as nanograms per microgram of tissue or nanograms per milliliter of a culture medium, for example. Alternatively, relative units can be employed to describe an expression level.

In a particular embodiment, when the measure of BAFF protein is performed by ELISA, the expression level of BAFF in a patient with a poor prognosis of the survival time or with a high risk of the recurrence of myocardial infarction is increased by at least 35%, preferably by at least 40%, preferably by at least 50%; preferably by at least 60%, preferably by at least 70%, preferably by at least 80%, more preferably by at least 90%, even more at least 100% compared to a control reference. In other words, preferably, when BAFF expression is measured by ELISA, the quantity of BAFF protein in a patient with a poor prognosis of the survival time or with a high risk of the recurrence of myocardial infarction is increased by at least 35%, preferably by at least 40%, preferably by at least 50%; preferably by at least 60%, preferably by at least 70%, preferably by at least 80%, more preferably by at least 90%, even more at least 100% compared to a control reference.

According to the invention, the inventors have established three tertiles useful to classify patients. Patients in the tertiles 2 or 3 have an increasing risk to die by myocardial infarction or an increasing risk to have a recurrent myocardial infarction (see example 1).

The present invention also relates to kits for predicting the survival time of a patient suffering of myocardial infarction or the recurrence of a myocardial infarction in a patient who has suffered from a myocardial infarction, comprising means for detecting BAFF expression.

According to the invention, the kits of the invention may comprise an anti-BAFF protein antibody; and another molecule coupled with a signalling system which binds to said BAFF protein antibody.

Typically, the antibodies or combination of antibodies are in the form of solutions ready for use. In one embodiment, the kit comprises containers with the solutions ready for use. Any other forms are encompassed by the present invention and the man skilled in the art can routinely adapt the form to the use in immunohistochemistry.

The present invention also relates to BAFF gene or protein as a biomarker for the prediction of the survival time of a patient suffering from myocardial infarction or the recurrence of a myocardial infarction in a patient who has suffered from a myocardial infarction.

In another embodiment, the invention relates to an in vitro method for monitoring a patient's response to myocardial infarction treatment which comprises a step of measuring the expression level of BAFF gene, or a step of measuring the level of BAFF protein, in a sample from a patient.

Thus, the present invention relates to the use of BAFF gene or protein as a biomarker for the monitoring of anti myocardial infarction therapies.

According to the invention, the expression level of BAFF gene or the level of BAFF protein may be determined to monitor a patient's response to myocardial infarction treatment.

Compounds and Uses Thereof

A second object of the invention relates to a compound which inhibits the binding of BAFF to TACI, BCMA or BAFF-R or a compound which is an inhibitor of BAFF, TACI, BCMA or BAFF-R gene expression for use in the improvement of heart function.

As used herein, the term "improvement of heart function" has its general meaning in the art and refers to an improvement of cardiac function/performance characterized by significant improvement in both post-ischemic ventricular remodeling (including size/dimensions, shape/geometry and structure of the ventricles) and myocardial function at systole (like ejection fraction) and/or diastole (like relaxation or compliance).

In one embodiment, the compound which inhibits the binding of BAFF to TACI, BCMA or BAFF-R or a compound which is an inhibitor of BAFF, TACI, BCMA or BAFF-R gene expression may be used in the improvement of heart function after myocardial infarction or acute myocardial infarction.

In another embodiment the compound which inhibits the binding of BAFF to TACI, BCMA or BAFF-R or the compound which is an inhibitor of BAFF, TACI, BCMA or BAFF-R gene expression may be useful for the improvement of heart function and thus for the improvement of heart function after myocardial infarction or acute myocardial infarction in a non-lupic patient.

Thus, the invention also relates to a compound which inhibits the binding of BAFF to TACI, BCMA or BAFF-R or a compound which is an inhibitor of BAFF, TACI, BCMA or BAFF-R gene expression for use in the improvement of heart function in a non-lupic patient.

As used herein, the term "TACI" (transmembrane activator and calcium-modulator and cyclophilin ligand interactor) has its general meaning in the art and refers to a transmembrane receptor protein found predominantly on the surface of B cells, which are an important part of the immune system. TACI is a lymphocyte-specific member of the tumor necrosis factor (TNF) receptor superfamily.

As used herein, the term "BCMA" (B cell maturation antigen) has its general meaning in the art and refers to member of the TNFR superfamily expressed on B cells.

As used herein, the term "BAFF-R" has its general meaning in the art and refers to a receptor expresses on all mature B cells.

In particular embodiment, the compound according to the invention inhibits the binding of BAFF to TACI.

In particular embodiment, the compound according to the invention inhibits the binding of BAFF to BCMA.

In particular embodiment, the compound according to the invention inhibits the binding of BAFF to BAFF-R.

In particular embodiment, the compound according to the invention is an inhibitor of BAFF gene expression.

In particular embodiment, the compound according to the invention is an inhibitor of TACI gene expression.

In particular embodiment, the compound according to the invention is an inhibitor of BCMA gene expression.

In particular embodiment, the compound according to the invention is an inhibitor of BAFF-R gene expression.

In another particular embodiment, the compound according to the invention is an inhibitor of BAFF to TACI, BCMA or BAFF-R signalling pathway.

In a particular embodiment, the compound which inhibits the binding of BAFF to TACI, BCMA or BAFF-R or a compound which is an inhibitor of BAFF, TACI, BCMA or BAFF-R gene expression may be used for the treatment of myocardial infarction.

In one embodiment, the myocardial infarction is an acute myocardial infarction.

In one embodiment, the compound according to the invention may bind to BAFF, TACI, BCMA or BAFF-R and block the binding of BAFF on TACI, BCMA or BAFF-R and block its physiological effects that is to say its effect on the monocyte mobilization or infiltration. To identify a compound able to block the interaction between BAFF, TACI, BCMA or BAFF-R, a test may be used. For example, the compound to test will compete with the binding of BAFF labelled with a flurochrome (as fluorescein isothiocyanate) on TACI, BCMA or BAFF-R transfected cell lines. The inhibition of the binding will then analyzed by flow cytometry.

As used herein, the term "inhibitor of the signaling pathway" denotes a compound which blocks the signaling cascade of a receptor that is to say the activation of molecules implicated in this pathway.

Typically, the compound according to the invention includes but is not limited to a small organic molecule, an antibody, and a polypeptide.

In one embodiment, the compound according to the invention may be a low molecular weight compound, e.g. a small organic molecule (natural or not).

The term "small organic molecule" refers to a molecule (natural or not) of a size comparable to those organic molecules generally used in pharmaceuticals. The term excludes biological macromolecules (e.g., proteins, nucleic acids, etc.). Particular small organic molecules range in size up to about 10000 Da, more preferably up to 5000 Da, more preferably up to 2000 Da and most preferably up to about 1000 Da.

In one embodiment, the compound according to the invention is an antibody. Antibodies directed against BAFF, TACI, BCMA or BAFF-R can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against BAFF, TACI, BCMA or BAFF-R can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-BAFF, anti-TACI, anti-BCMA or anti-BAFF-R single chain antibodies. Compounds useful in practicing the present invention also include anti-BAFF, anti-TACI, anti-BCMA or anti-BAFF-R antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to BAFF, TACI, BCMA or BAFF-R.

Humanized anti-BAFF, anti-TACI, anti-BCMA or anti-BAFF-R antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then, for this invention, neutralizing antibodies of BAFF, TACI, BCMA or BAFF-R are selected.

In one embodiment, the compound according to the invention is an anti-BAFF antibody.

In a particular embodiment, the antibody according to the invention may be the Belimumab (see for example Espinosa G. et al, 2010 or Liu Zheng et al., 2011).

In a particular embodiment, the antibody according to the invention may be an antibody according to Scholz L. Jean et al., 2008.

In a particular embodiment, the antibody according to the invention may be the LY2127399 (see for example Davidson A 2010).

In a particular embodiment, the antibody according to the invention may be an antibody according to the patent application WO0043032.

In a particular embodiment, the antibody according to the invention may be an antibody according to the patent application WO2006025345.

In a particular embodiment, the antibody according to the invention may be an antibody according to the patent application WO2006025345.

In a particular embodiment, the antibody according to the invention may be an antibody according to the patent application CN101851291.

In another embodiment, the compound according to the invention is an anti-TACI antibody.

In a particular embodiment, the antibody according to the invention may be an antibody according to the patent application WO02066516.

In a particular embodiment, the antibody according to the invention may be an antibody according to the patent application WO2004011611.

In a particular embodiment, the antibody according to the invention may be an antibody according to the patent application WO0160397.

In another embodiment, the compound according to the invention is an anti-BCMA antibody.

In a particular embodiment, the antibody according to the invention may be an antibody according to the patent application WO02066516.

In a particular embodiment, the antibody according to the invention may be an antibody according to the patent application WO0124811.

In a particular embodiment, the antibody according to the invention may be an antibody according to the patent application WO0160397.

In another embodiment, the compound according to the invention is an anti-BAFF-R antibody.

In a particular embodiment, the antibody according to the invention may be an antibody according to Ramanujam Meera et al., 2006.

In a particular embodiment, the antibody according to the invention may be an antibody according to Rauch Melanie et al., 2009.

In one embodiment, the compound according to the invention is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Then, for this invention, neutralizing aptamers of BAFF, TACI, BCMA or BAFF-R are selected.

In one embodiment, the compound according to the invention is a polypeptide.

In a particular embodiment the polypeptide is a functional equivalent of TACI, BCMA or BAFF-R. As used herein, a "functional equivalent" of TACI, BCMA or BAFF-R is a compound which is capable of binding to BAFF, thereby preventing its interaction with TACI, BCMA or BAFF-R. The term "functional equivalent" includes fragments, mutants, and muteins of TACI, BCMA or BAFF-R. The term "functionally equivalent" thus includes any equivalent of TACI, BCMA or BAFF-R obtained by altering the amino acid sequence, for example by one or more amino acid deletions, substitutions or additions such that the protein analogue retains the ability to bind to BAFF. Amino acid substitutions may be made, for example, by point mutation of the DNA encoding the amino acid sequence.

Functional equivalents include molecules that bind BAFF and comprise all or a portion of the extracellular domains of TACI, BCMA or BAFF-R. Typically, said functional equivalents may be the extracellular domains of TACI, BCMA or BAFF-R expressed as Fc fusion protein. For example, fusion proteins may be composed of the extracellular ligand binding portion of TACI which blocks activation of TACI by BAFF (e.g. Atacicept, Merck) or a fusion protein composed of the extracellular ligand-binding portion of BAFF-R which blocks activation of BAFF-R by BAFF (e.g. BR3-Fc, Biogen and Genentech, see for example Vugmeyster Yulia et al., 2006). Such fusion proteins can be generated using methods known in the art, such as recombinant DNA technology as is described in details herein below.

In one embodiment, the polypeptide according to the invention is able to improve hear function and treat myocardial infarction through its properties of decoy receptor.

By "decoy receptor", is meant that the polypeptide according to the invention trap BAFF and prevent its physiological effects on TACI, BCMA or BAFF-R.

The functional equivalents include soluble forms of TACI, BCMA or BAFF-R. A suitable soluble form of these proteins, or functional equivalents thereof, might comprise, for example, a truncated form of the protein from which the transmembrane domain has been removed by chemical, proteolytic or recombinant methods.

Preferably, the functional equivalent is at least 80% homologous to the corresponding protein. In a particular embodiment, the functional equivalent is at least 90% homologous as assessed by any conventional analysis algorithm such as for example, the Pileup sequence analysis software (Program Manual for the Wisconsin Package, 1996).

The term "a functionally equivalent fragment" as used herein also may mean any fragment or assembly of fragments of TACI, BCMA or BAFF-R that binds to BAFF. Accordingly the present invention provides a polypeptide capable of inhibiting binding of TACI, BCMA or BAFF-R to BAFF, which polypeptide comprises consecutive amino acids having a sequence which corresponds to the sequence of at least a portion of an extracellular domain of TACI, BCMA or BAFF-R, which portion binds to BAFF. In one embodiment, the polypeptide corresponds to an extracellular domain of TACI, BCMA or BAFF-R. In another embodiment, the polypeptide corresponds to the extracellular domains of TACI, BCMA or BAFF-R expressed as Fc fusion protein.

Functionally equivalent fragments may belong to the same protein family as the TACI, BCMA or BAFF-R identified herein. By "protein family" is meant a group of proteins that share a common function and exhibit common sequence homology. Homologous proteins may be derived from non-human species. Preferably, the homology between functionally equivalent protein sequences is at least 25% across the whole of amino acid sequence of the complete protein. More preferably, the homology is at least 50%, even more preferably 75% across the whole of amino acid sequence of the protein or protein fragment. More preferably, homology is greater than 80% across the whole of the sequence. More preferably, homology is greater than 90% across the whole of the sequence. More preferably, homology is greater than 95% across the whole of the sequence.

In one embodiment, the polypeptide according to the invention may be also a functional equivalent of BAFF. As used herein, a "functional equivalent" of BAFF is a compound which is capable of binding to TACI, BCMA or BAFF-R, thereby preventing its interaction with the natural ligand BAFF. The term "functional equivalent" includes fragments, mutants, and muteins of BAFF. The term "functionally equivalent" thus includes any equivalent of BAFF obtained by altering the amino acid sequence, for example by one or more amino acid deletions, substitutions or additions such that the protein analogue retains the ability to bind to TACI, BCMA or BAFF-R. Amino acid substitutions may be made, for example, by point mutation of the DNA encoding the amino acid sequence. A compound as explained in the patent applications WO2004081043 or WO2006034106 may be used.

The polypeptides of the invention may be produced by any suitable means, as will be apparent to those of skill in the art. In order to produce sufficient amounts of BAFF, TACI, BCMA or BAFF-R or functional equivalents thereof for use in accordance with the present invention, expression may conveniently be achieved by culturing under appropriate conditions recombinant host cells containing the polypeptide of the invention. Preferably, the polypeptide is produced by recombinant means, by expression from an encoding nucleic acid molecule. Systems for cloning and expression of a polypeptide in a variety of different host cells are well known.

When expressed in recombinant form, the polypeptide is preferably generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E. coli*.

In specific embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. In example adding dipeptides can improve the penetration of a circulating agent in the eye through the blood retinal barrier by using endogenous transporters.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the protein or fragment of the protein described herein for therapeutic delivery.

In another embodiment, the compound according to the invention is an inhibitor of BAFF, TACI, BCMA or BAFF-R gene expression.

Small inhibitory RNAs (siRNAs) can also function as inhibitors of BAFF, TACI, BCMA or BAFF-R expression for use in the present invention. BAFF, TACI, BCMA or BAFF-R gene expression can be reduced by contacting a subject or cell with a small double stranded RNA (dsRNA), or a vector or construct causing the production of a small double stranded RNA, such that BAFF, TACI, BCMA or BAFF-R gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of BAFF, TACI, BCMA or BAFF-R gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of BAFF, TACI, BCMA or BAFF-R mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of BAFF, TACI, BCMA or BAFF-R gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing BAFF, TACI, BCMA or BAFF-R. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Particular viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Particular viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a particular embodiment, the antisense oligonucleotide, siRNA, shRNA or ribozyme nucleic acid sequence is under the control of a heterologous regulatory region, e.g., a heterologous promoter. The promoter may be specific for Muller glial cells, microglia cells, endothelial cells, pericyte cells and astrocytes For example, a specific expression in Muller glial cells may be obtained through the promoter of the glutamine synthetase gene is suitable. The promoter can also be, e.g., a viral promoter, such as CMV promoter or any synthetic promoters.

Another object of the invention relates to a method for use in the improvement of heart function comprising administering to a subject in need thereof a therapeutically effective amount of a compound which inhibits the binding of BAFF to TACI, BCMA or BAFF-R or a compound which is an inhibitor of BAFF, TACI, BCMA or BAFF-R gene expression or signalling pathway as described above.

In one embodiment, the invention relates to a method for treating myocardial infarction comprising administering to a subject in need thereof a therapeutically effective amount of a compound which inhibits the binding of BAFF to TACI, BCMA or BAFF-R or a compound which is an inhibitor of BAFF, TACI, BCMA or BAFF-R gene expression or signalling pathway as described above.

In one aspect, the invention relates to a method for treating myocardial infarction comprising administering to a subject in need thereof a therapeutically effective amount of an antibody anti-BAFF like the belimumab.

As used herein, the term "treating" or "treatment", denotes reversing, alleviating, inhibiting the progress of, or preventing the disorder or condition to which such term applies, or reversing, alleviating, inhibiting the progress of, or preventing one or more symptoms of the disorder or condition to which such term applies.

In another embodiment, the myocardial infarction is an acute myocardial infarction.

Another object of the invention relates to a method for treating patient who has been considered as a poor prognosis for the survival time or as a high risk for the recurrence of a myocardial infarction according to the above method of the invention comprising administering to a subject in need thereof a compound which inhibits the binding of BAFF to TACI, BCMA or BAFF-R or a compound which is an inhibitor of BAFF, TACI, BCMA or BAFF-R gene expression or signaling pathway as described above or a B cell depleting agent.

Another object of the invention relates to a compound which inhibits the binding of BAFF to TACI, BCMA or BAFF-R or a compound which is an inhibitor of BAFF, TACI, BCMA or BAFF-R gene expression or signaling pathway or a B cell depleting agent for use in the treatment of patient who has been considered as a poor prognosis for the survival time or as a high risk for the recurrent of a myocardial infarction according to the above method of the invention.

In a particular embodiment and according to the methods of treatment of the invention the patient is a non-lupic patient.

A "B cell depleting agent" has its general meaning in the art and refers to a molecule which depletes or destroys B cells in a patient and thus reduces the humoral response elicited by the B cell. B cell depleting agents are well known in the art (Thomas Dörner, Peter E Lipsky, B-cell targeting: a novel approach to immune intervention today and tomorrow, Expert Opinion on Biological Therapy September 2007, Vol. 7, No. 9, Pages 1287-1299: 1287-1299). The B cell depleting agent may bind to a B cell surface marker. A "B cell surface marker" or "B cell target" or "B cell antigen" herein is an antigen expressed on the surface of a B cell which can be targeted with a B cell depleting agent which binds thereto. Exemplary B cell surface markers include CD10, CD 19, CD20, CD21, CD22, CD23, CD24, CD37, CD53, CD72, CD73, CD74, CDw75, CDw76, CD77, CDw78, CD79a, CD79b, CD80, CD81, CD82, CD83, CDw84, CD85 and CD86.

In a particular embodiment, the B cell depleting agent is an anti-B cell antibody, preferably a monoclonal antibody (e.g. a chimeric, humanized or human antibody). For example, a suitable anti-B cell antibody can be an antibody targeting any B cell surface marker e.g. an antiCD20 monoclonal antibody [e.g. Rituximab (Roche), Ibritumomab tiuxetan (Bayer Schering), Tositumomab (GlaxoSmithKline), AME-133v (Applied Molecular Evolution), Ocrelizumab (Roche), Ofatumumab (HuMax-CD20, Gennab), TRU-015 (Trubion) and IMMU-106 (Immunomedics)], an anti-CD22 antibody [e.g. Epratuzumab, Leonard et al., Clinical Cancer Research (Z004) 10: 53Z7-5334], an anti-CD79a antibody, an anti-CD27 antibody, or an antiCDl9 antibody (e.g. U.S. Pat. No. 7,109,304). Another example of anti-B cell antibody include an antibody targeting a B cell survival factor or a cytokine imperative for B cell function or an effector thereof (e.g., a receptor which binds the aforementioned factor). Such antibodies include the anti-APRIL antibody (e.g. anti-human APRIL antibody, ProSci inc.), the anti-IL-6 antibody [previously described by De Benedetti et al., J Immunol (2001) 166: 4334-4340 and by Suzuki et al., Europ J of Immunol (1992) 22 (8) 1989-1993, fully incorporated herein by reference], the anti-IL-7 antibody (R&D Systems, Minneapolis, Minn.) or the SDF-1 antibody (R&D Systems, Minneapolis, Minn.).

Depletion of B cells may also be achieved by the use of fusion proteins which block activation of B cell receptors. For example, a fusion protein composed of the extracellular ligand binding portion of TACI which blocks activation of TACI by April and BLyS (e.g. Atacicept, Merck) or a fusion protein composed of the extracellular ligand-binding portion of BAFF-R which blocks activation of BAFF-R by BLys (e.g. BR3-Fc, Biogen and Genentech). Such fusion proteins can be generated using methods known in the art, such as recombinant DNA technology as is described in details herein below.

Typically, a "B cell depleting agent" may be an agent as described in Gullick Nicola et al. 2007.

In another embodiment, the B cell depleting agent is a B cell depleting antibody.

In still another embodiment, the B cell depleting agent is an anti-CD20 antibody.

In another object, the invention relates to a compound which inhibits the binding of BAFF to TACI, BCMA or BAFF-R or the compound which is an inhibitor of BAFF, TACI, BCMA or BAFF-R gene expression or signalling pathway for use in the improvement of heart function after myocardial infarction or acute myocardial infarction.

Pharmaceutical Composition

Another object of the invention relates to a therapeutic composition comprising a compound according to the invention for use in the in the improvement of heart function.

In another embodiment, invention relates to a therapeutic composition comprising a compound according to the invention for use in treatment of myocardial infarction.

Preferably, said compound is an inhibitor of the binding of BAFF to TACI, BCMA or BAFF-R or an inhibitor of BAFF, TACI, BCMA or BAFF-R gene expression or signaling pathway.

In a particular embodiment, the invention relates to a therapeutic composition comprising a compound which inhibits the binding of BAFF to TACI, BCMA or BAFF-R or a compound which is an inhibitor of BAFF, TACI, BCMA or BAFF-R gene expression or signaling pathway or a B cell depleting agent for use in the treatment of patient who has been considered as a poor prognosis for the survival time or as a high risk for the recurrent of a myocardial infarction according to the above method of the invention.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

Compounds of the invention may be administered in the form of a pharmaceutical composition, as defined below.

By a "therapeutically effective amount" is meant a sufficient amount of compound to treat and/or to prevent myocardial infarction.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The invention will be further illustrated by the following figures and examples. However, these examples and figures should not be interpreted in any way as limiting the scope of the present invention.

EXAMPLE

Example 1

Elevated circulating level of Baff at the acute phase of MI is associated with adverse cardiovascular outcome.

The inventors assess the relationship between circulating Baff level and clinical outcomes in a cohort of 1000 patients admitted for acute MI. The risk of death and recurrent MI was associated with increasing tertiles of circulating Baff at admission. The HR of death and recurrent MI in the second and third tertiles of Baff were 1.65 (1.05-2.58) and 3.14 (2.09-4.73) compared with the lowest tertile (p<0.0001). The association remained significant in a fully adjusted model (FIG. 1).

Example 2

Blockade of Baff signaling impairs monocyte mobilization and improves heart function after acute MI.

Figure 2:
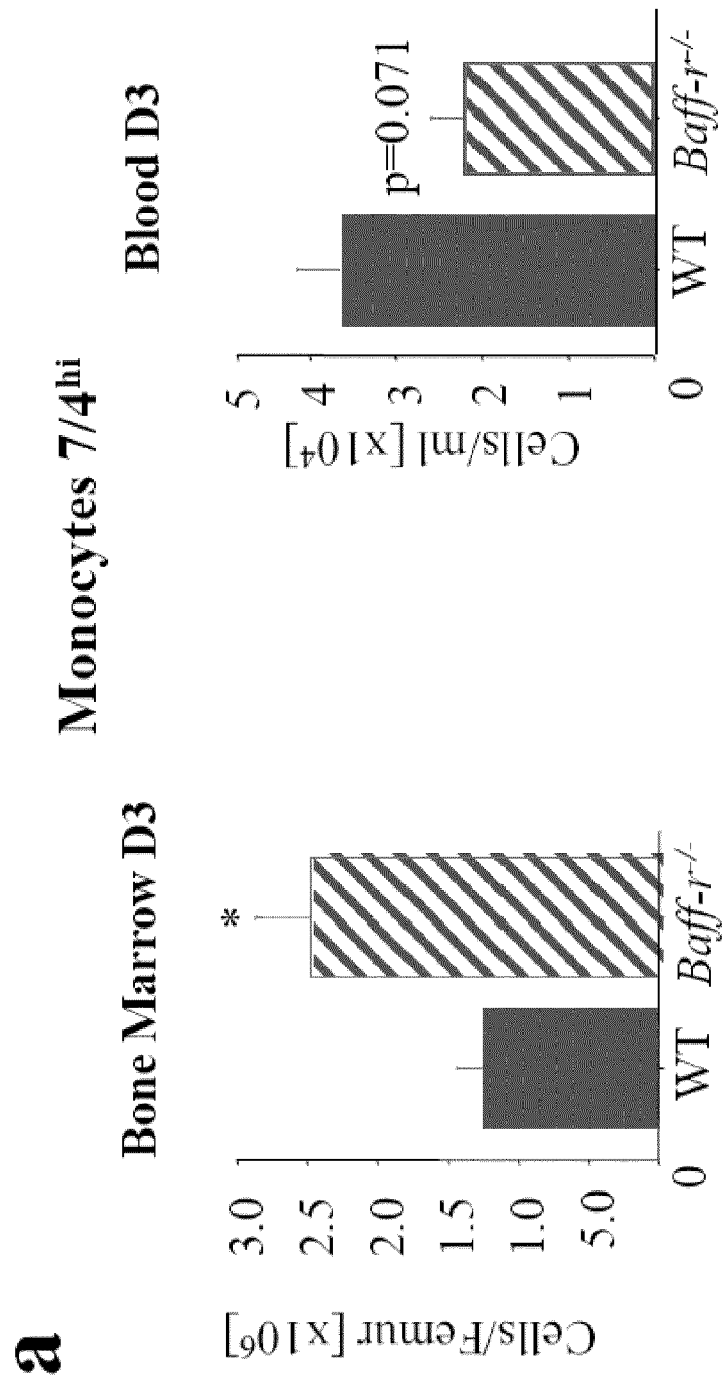
FIG. 2A-E. Blockade of Baff signaling impairs monocyte mobilization and improves heart function after acute MI. (a) Quantification of the number of 7/4hi monocytes in the bone marrow (left) and in the blood (right) of Baff-r−/− mice compared to controls on day 3 after MI. (b) Quantitative analysis of the shortening fraction (%) of Baff-r−/− mice compared to Baff-r+/+ and Baff-r+/− mice at day 14 post-MI. Data are representative of 8 to 11 mice per group. Mean values .+-.SEM are shown. * P<0.05 and ** P<0.01. (c, d) Quantification of the number of B220+IgM+B cells (d) and 7/4hi monocytes (d) in blood of anti-Baff treated mice compared to PBS injected animals. (e) Quantitative analysis of the shortening fraction (%) of anti-Baff treated mice compared to PBS at day 14 post-MI (n=12 to 15 mice per group). * P<0.05, P<0.01, *P<0.001.

Baff signaling through Baff receptor (Baff-r) is required for the maintenance of mature B2 cells and Baff-r–/– mice are characterized by a profound reduction of follicular (FO) and marginal zone (MZ) B lymphocytes but preservation of B1 cells. We therefore addressed the impact of Baff-r deficiency on the pathophysiology of post-ischemic myocardial injury. Interestingly, we found that Baff-r–/– mice showed a significant increase in the accumulation of Ly6Chi monocytes in the bone marrow but displayed lower levels of these monocytes in the circulating blood compared with control littermates, clearly suggesting impaired monocytes mobilization (FIG. 2a). Importantly, Baff-r deficiency improved heart function after MI as shown by the significant increase of shortening fraction in Baff-r–/– mice compared with Baff-r+/– littermates (FIG. 2b). To further substantiate the role of Baff in this context, we treated a group of wild-type mice with anti-Baff monoclonal antibody. We found that Baff neutralization led to significant depletion of circulating B lymphocytes (FIG. 2c), which was associated with impaired Ly6Chi monocyte mobilization (FIG. 2d) and improved cardiac function (FIG. 2e).

REFERENCES

Throughout this application, various references describe the state of the art to which this invention pertains. The disclosures of these references are hereby incorporated by reference into the present disclosure.

Ait-Oufella, H., et al. B cell depletion reduces the development of atherosclerosis in mice. J Exp Med 207, 1579-1587 (2010).

Armstrong, P. W., et al. Pexelizumab for acute ST-elevation myocardial infarction in patients undergoing primary percutaneous coronary intervention: a randomized controlled trial. JAMA 297, 43-51 (2007).

Busche, M. N., Pavlov, V., Takahashi, K. & Stahl, G. L. Myocardial ischemia and reperfusion injury is dependent on both IgM and mannose-binding lectin. Am J Physiol Heart Circ Physiol 297, H1853-1859 (2009).

Cazes, A., et al. Mechanical ventricular assistance in heart failure: pathology of the cardiac apex removed during device implantation. Cardiovasc Pathol 19.112-116 (2010).

Cochain, C., et al. Regulation of monocyte subset systemic levels by distinct chemokine receptors controls post-ischaemic neovascularization. Cardiovasc Res 88, 186-195 (2010).

Eikelboom, J. W. & O'Donnell, M. Pexelizumab does not "complement" percutaneous coronary intervention in patients with ST-elevation myocardial infarction. JAMA 297, 91-92 (2007).

Granger, D. N. & Korthuis, R. J. Physiologic mechanisms of postischemic tissue injury. Annu Rev Physiol 57, 311-332 (1995).

Granger, C. B., et al. Pexelizumab, an anti-CS complement antibody, as adjunctive therapy to primary percutaneous coronary intervention in acute myocardial infarction: the COMplement inhibition in Myocardial infarction treated with Angioplasty (COMMA) trial. Circulation 108, 1184-1190 (2003).

Gullick Nicola & D'Cruz David. New therapies for the treatment of systemic lupus erythematosus. Expert Opin. Ther. Patents (2007) 17(3).

Haas, M. S., et al. Blockade of self-reactive IgM significantly reduces injury in a murine model of acute myocardial infarction. Cardiovasc Res 87, 618-627 (2010). Leuschner, F., et al. Rapid monocyte kinetics in acute myocardial infarction are sustained by extramedullary monocytopoiesis. J Exp Med 209, 123-137 (2012).

Mahaffey, K. W., et al. Effect of pexelizumab, an anti-CS complement antibody, as adjunctive therapy to fibrinolysis in acute myocardial infarction: the COMPlement inhibition in myocardial infarction treated with thromboLYtics (COMPLY) trial. Circulation 108, 1176-1183 (2003).

Nahrendorf, M., et al. The healing myocardium sequentially mobilizes two monocyte subsets with divergent and complementary functions. J Exp Med 204, 3037-3047 (2007).

Shah, A. M. & Mann, D. L. In search of new therapeutic targets and strategies for heart failure: recent advances in basic science. Lancet 378, 704-712 (2011).

Uchida, J., et al. Mouse CD20 expression and function. Int Immunol 16, 119-129 (2004).

Vinten-Johansen, J. Involvement of neutrophils in the pathogenesis of lethal myocardial reperfusion injury. Cardiovasc Res 61, 481-497 (2004).

White, H. D. & Chew, D. P. Acute myocardial infarction. Lancet 372, 570-584 (2008).

The invention claimed is:

1. A method for predicting the survival time of a patient suffering from myocardial infarction or the recurrence of a myocardial infarction in a patient who has suffered from a myocardial infarction and treating said patient, comprising the steps of
   i) determining the expression level of B cell activating factor (BAFF) in a sample from said patient,
   ii) comparing said expression level with a control value, wherein said control value is based on BAFF levels in a collection of samples from patients suffering from myocardial infarction, or based on BAFF levels in a collection of samples from healthy subjects,
   iii) providing a good prognosis of the survival time or a low risk of the recurrence of a myocardial infarction when the expression level is lower than the control value,
   or providing a poor prognosis of the survival time or a high risk of the recurrence of a myocardial infarction when the expression level is higher than the control value, and
   iv) administering a therapeutically effective amount of an anti-CD20 antibody to said patient when a poor prognosis is provided in step iii), wherein the therapeutically effective amount is sufficient to treat said patient.

2. The method according to claim 1, wherein the patient is a non-lupic patient.

3. The method according to claim 1, wherein said sample is selected from the group consisting of blood, plasma, serum, lymph and cardiac tissue.

* * * * *